United States Patent [19]
Steinberg

[11] Patent Number: 5,630,783
[45] Date of Patent: May 20, 1997

[54] PORTABLE CYSTOSCOPE

[76] Inventor: Jeffrey Steinberg, 39 Border Rd., Needham, Mass. 02192

[21] Appl. No.: 514,193

[22] Filed: Aug. 11, 1995

[51] Int. Cl.$^6$ .................................................. A61B 1/00
[52] U.S. Cl. ............................ 600/158; 604/26; 600/160
[58] Field of Search ............................ 600/146, 156, 600/158, 153, 178, 179, 199, 249; 128/205.21; 604/26

[56] References Cited

U.S. PATENT DOCUMENTS

| | | |
|---|---|---|
| 1,345,406 | 7/1920 | Rimmer. |
| 2,279,714 | 4/1942 | Meyerhof et al.. |
| 2,325,831 | 8/1943 | Cameron. |
| 2,428,425 | 10/1947 | Levitt ........................... 128/205.21 X |
| 2,623,519 | 12/1952 | Cohen ............................. 128/200.19 |
| 3,315,207 | 4/1967 | Speelman ........................ 600/199 X |
| 4,258,721 | 3/1981 | Parent et al. ........................ 600/158 |
| 4,404,963 | 9/1983 | Kohri. |
| 4,586,491 | 5/1986 | Carpenter. |
| 4,598,698 | 7/1986 | Siegmund ........................ 604/26 X |
| 4,607,619 | 8/1986 | Seike et al. ........................ 600/153 |
| 4,712,537 | 12/1987 | Pender ........................... 600/200 |
| 5,133,336 | 7/1992 | Savitt et al. ..................... 600/158 X |
| 5,255,668 | 10/1993 | Umeda ........................... 600/146 X |
| 5,292,346 | 3/1994 | Ceravolo ........................ 600/179 X |
| 5,349,947 | 9/1994 | Newhouse et al. ................ 128/203.21 |
| 5,447,148 | 9/1995 | Oneda et al. ..................... 600/158 X |

FOREIGN PATENT DOCUMENTS 400267  12/1990  European Pat. Off. ............... 600/178

OTHER PUBLICATIONS

Product literature sheet for Olympus CYF-3, Olympus Optical Co., Ltd.
Product literature sheet for Port-O-Scope, North American Medical Products, Inc.

*Primary Examiner*—Stephen R. Crow
*Assistant Examiner*—David R. Risley
*Attorney, Agent, or Firm*—Cesari and McKenna, LLP

[57] ABSTRACT

A portable cystoscope or endoscope provides a handle and an elongated tube that extends distally from the handle. A viewing port having an eye piece or camera is located on the handle, typically adjacent a proximal end. A viewing conduit is in optical communication with the viewing port and extends through the handle and tube, to the distal end of the tube. A light source, which can include a battery, is mounted entirely on and is carried by the handle. A light conduit extends from the light source through the tube so that it projects illuminating light from the distal end of the tube. A gas source is located on the handle, typically within a compartment in the handle, and in communication with a gas conduit that extends from the gas source to an outlet at the distal end of the tube. The gas source can comprise a $CO_2$ cartridge and it enables insufflation of the area within the body to be viewed for enhanced viewing.

18 Claims, 6 Drawing Sheets

PORTABLE CYSTOSCOPE

FIELD OF THE INVENTION

This invention relates to a cystoscope or endoscope and more particularly to a cystoscope or endoscope having enhanced portability.

BACKGROUND OF THE INVENTION

Cystoscopes and endoscopes are commonly used in a variety of procedures in which the physician must visually examine an internal portion of the body. Cystoscopes, in particular, are used by urologists to examine the urethra and bladder to diagnose urethral, prostate and bladder abnormalities. The cystoscope enables the internal regions of the urinary tract to be inspected, without the need for painful incisions, by enabling the viewer to insert a distal portion of the cystoscope through the urethra from whence it is moved to its final location within the urinary tract.

Figure 1:
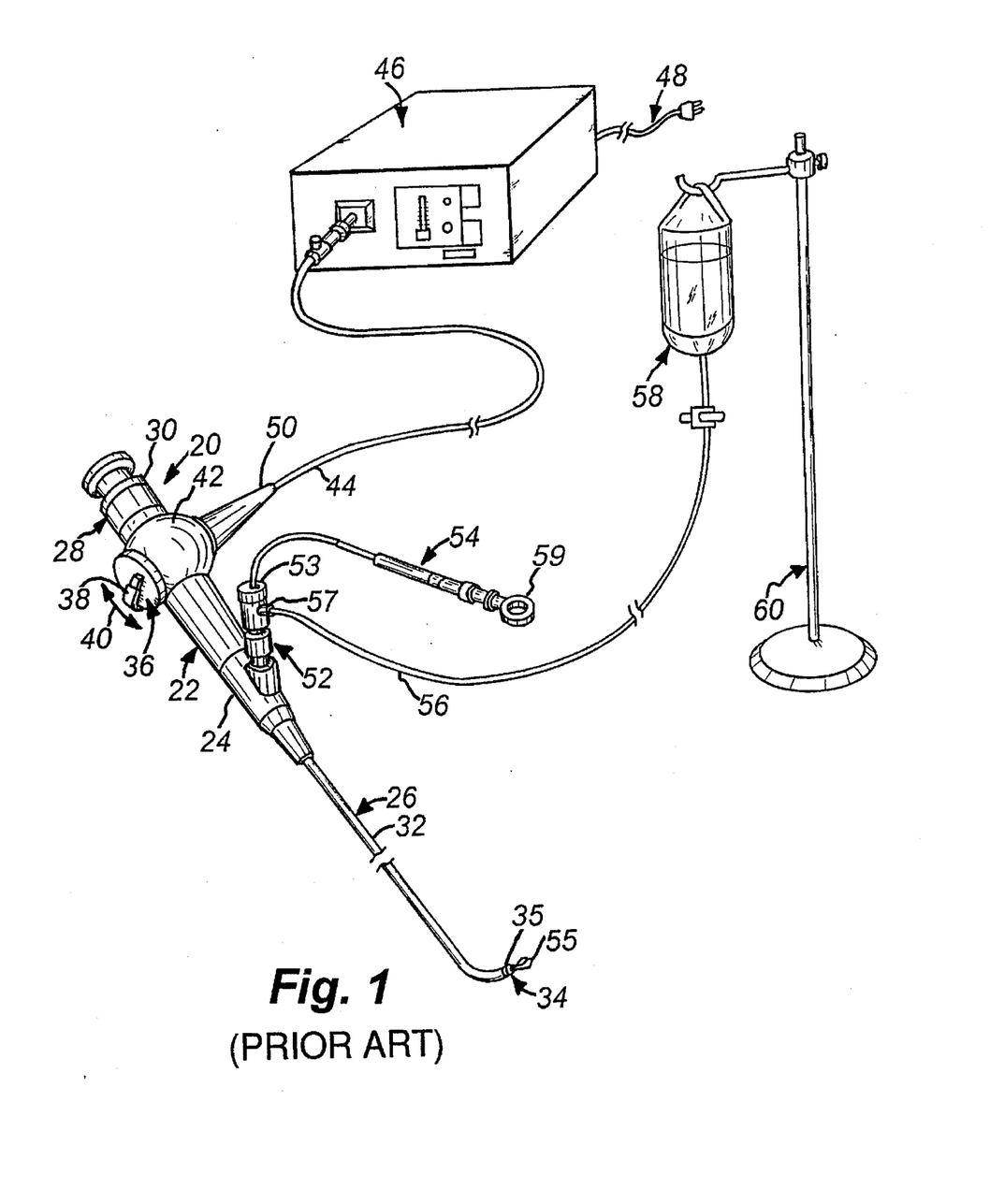
FIG. 1 is a perspective view of a cystoscopic system according to the prior art.

A cystoscope according to the prior art is detailed in FIG. 1. The cystoscope 20 includes a housing or handle 22 having an elongated distal portion 24 that supports a flexible tube 26. The handle 22 also includes an eye piece 28 at the proximal end of the handle 22. The eye piece 28 can include a zoom adjustment knob and/or a focus knob 30. Alternatively, the eye piece 28 can be substituted with a video camera for remote viewing. The tube 26 can vary in length, but is typically sized to penetrate the bladder through the urethra via the end of the penis. The tube 26 typically includes an outer covering 32 constructed from a low-friction polymer such as Teflon® or polyethelene. The tube can include an internal web or mesh that provides the tube 26 with a semi-rigid characteristic and protects the inner components. The distal end 34 of the tube 26 typically includes a polished metal end cap 35 having a plurality of exit ports which are described below.

The handle 22 includes a movable steering control 36 with a steering lever or knob 38. The steering lever moves (arrow 40) proximally and distally along the handle to control a pair of steering cables (not shown) within the tube 26. The steering cables enable the distal end 34 of the tube 26 to bend so that the tube 26 can negotiate bends and corners within the urinary tract as it is driven distally inward toward the bladder.

The steering control 36 is mounted on an enlarged ball 42 located between the proximal end and the distal end of the handle 22. The ball 42 is interconnected with a fiber optic light source cable 44 that communicates with a light source 46 according to the prior art. The light source 46 is, typically, a variable-intensity halogen lamp that draws power from a conventional 110 VAC power source via an electrical cord 48. An associated internal fiber optic cable (not shown) interconnects within the ball 42 of the handle 22 with the light source cable 44. A connector 50 is used to join the internal fiber optic cable (not shown) with the source cable 44. The internal fiber optic cable extends through the distal end 24 of the handle 22 and passes along the full length of the tube 26, and is exposed at the distal end 34 of the tube 26 to provide light at the distal end.

The tube 26 also includes a bundle of viewing fiber optic cables (not shown) that are also exposed at the distal end 34 of the tube 26. The viewing fiber optic cables (not shown) are connected with the eye piece 28 and transmit an image illuminated by the light source 46 from the distal end to the viewer.

According to the prior art, an irrigation/instrument assembly 52 or other fitting is provided at the distal end 24 of the handle 22. The assembly 52 interconnects with an internal tubing (not shown) that exits at the distal end 34 of the tube 26. The assembly 52 includes an instrument port 53 that provides a conduit for guiding an actuating mechanism of an instrument such as the grasper 55 located at the tube's distal end 34. A remote plunger assembly 54 with a movable finger control 59 controls the grasper 55. The irrigation/instrument assembly 52 also includes a fluid inlet 57 that can comprise a Luer-style fitting connected with a sterile tubing 56 that, in this embodiment, terminates in a source of sterile saline or water 58 suspended from a stand 60. According to the prior art, saline or sterile water 58 is used to distend the bladder and provide a fluidic light conduit that enhances the viewing environment by providing an enlarged viewing area with enhanced light transmission. Both instruments and fluid can pass down a single internal tubing (not shown) to exit at the distal end 34.

A disadvantage of the cystoscope 20, according to the prior art, is that the external light source 46 and stand-mounted saline source 58 are bulky, require additional space, and are difficult to transport. In addition, the external light source is an expensive component that is dependent upon a source of household current for power. Likewise, a bag or bottle of saline or sterile water is relatively expensive and substantial quantities must be stored and carried if a multiplicity of examinations are undertaken. These added external components, hence, limit the use of the prior art cystoscope 20 at remote sites. Additionally, the external components increase the set up time for the cystoscope, thus reducing the available time for performing examinations.

In view of the disadvantages of the prior art, it is an object of this invention to provide a portable cystoscope or endoscope that does not require an external source of saline or sterile water and that is internally illuminated. The cystoscope should adequately perform all functions associated with a cystoscope or endoscope having an external light source. The cystoscope or endoscope should include a mechanism for distending the urinary tract without the need of costly and bulky sources of fluid. The distension mechanism should be self-contained within the cystoscope or endoscope housing and should be usable for plurality of examinations without servicing.

SUMMARY OF INVENTION

This invention relates to a portable cystoscope or endoscope that eliminates the need for a separate or external illumination and insufflation source, resulting in a more compact structure that is easy to set up and easily portable. The cystoscope or endoscope incorporates a self-contained light source with a rechargeable battery and a replaceable gas cartridge that is seated within the handle of the cystoscope or endoscope.

According to a preferred embodiment, the cystoscope or endoscope comprises a handle and an elongated tube that extends distally from the handle. A viewing port having an eye piece or a camera is also located on the handle. A viewing conduit is located in optical communication with the viewing port. The conduit extends through the handle to the distal end of the tube. A light source is mounted entirely on, and is carried by, the handle and is in communication with a light conduit that extends from the light source through the tube. The light source projects an illuminating light from the distal end of the tube. The handle also includes a gas source, and a gas conduit that extends from the gas source, through the tube, to an outlet located at the distal end of the tube.

The gas source can comprise a replaceable $CO_2$ cartridge held within a compartment in the handle that is accessible by a movable door. The door can include a base that forces the cartridge onto a puncturing nipple that opens the end of the cartridge and places it into a sealed relationship with the gas conduit.

The light conduit and the viewing conduit can each comprise fiber optic cables constructed from a single strand or from bundles of smaller cables. A separate conduit for directing liquid and/or instruments to the distal end can be provided. The conduit can include a fluid fitting on the handle and can be coupled to the gas conduit to enable fluid to be transferred through the gas conduit to the distal end of the tube.

The light source can include a removable battery that is fixed to the handle by a locking structure. The battery can be constructed so that it is placeable in a recharging unit at predetermined times. The battery can be formed within a housing that can include an on/off switch that controls a light bulb interconnected with the light conduit. Likewise, a control valve can be provided on the handle for controlling the flow of gas along the gas conduit. The teachings described herein, while particularly suited to a cystoscope or endoscope, can be applied to any portable viewing device in which illumination/and or insufflation are utilized.

BRIEF DESCRIPTION OF THE DRAWINGS

The foregoing and other objects and advantages of the invention will become more clear with reference to the following detailed description as illustrated by the drawings in which.

DETAILED DESCRIPTION

Figure 2:
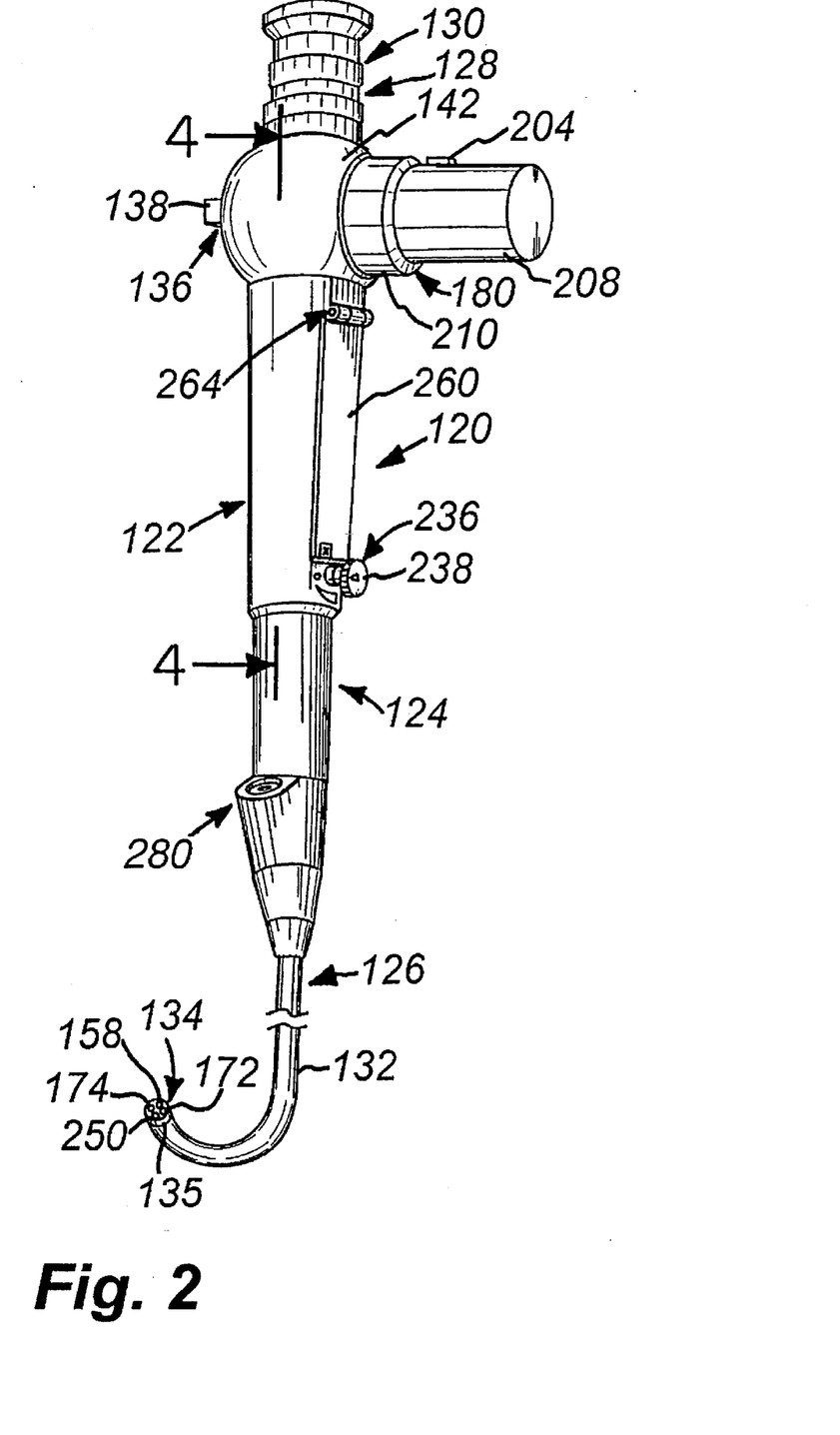
FIG. 2 is a perspective view of a cystoscope or endoscope according to this invention.

A cystoscope 120 according to this invention is shown, in overall detail, in FIG. 2. For the purpose of this description, the term "cystoscope" is used. However, this term is specifically intended to include an endoscope, hysteroscope, laryngoscope, or other examination device having a handle or housing and a flexible tube that extends distally from the housing for insertion into the interior of a body.

The external housing of the cystoscope 120 is similar in size and shape to the cystoscope 20 of the prior art (FIG. 1). The cystoscope 120 includes a body or housing 122 having a distal end 124 and a proximal eye piece 128. The eye piece 128 includes an adjustment or focus ring 130. The eye piece can be substituted with a video camera for remote imaging. The distal end 124 of the housing 122 supports a semi-rigid, flexible, tube 126 that is described further below. The tube 126 is covered with a flexible, low friction, sheathing 132 and includes a distal end 134 having a polished metallic ring 135 with a series of openings that are described further below.

Figure 3:
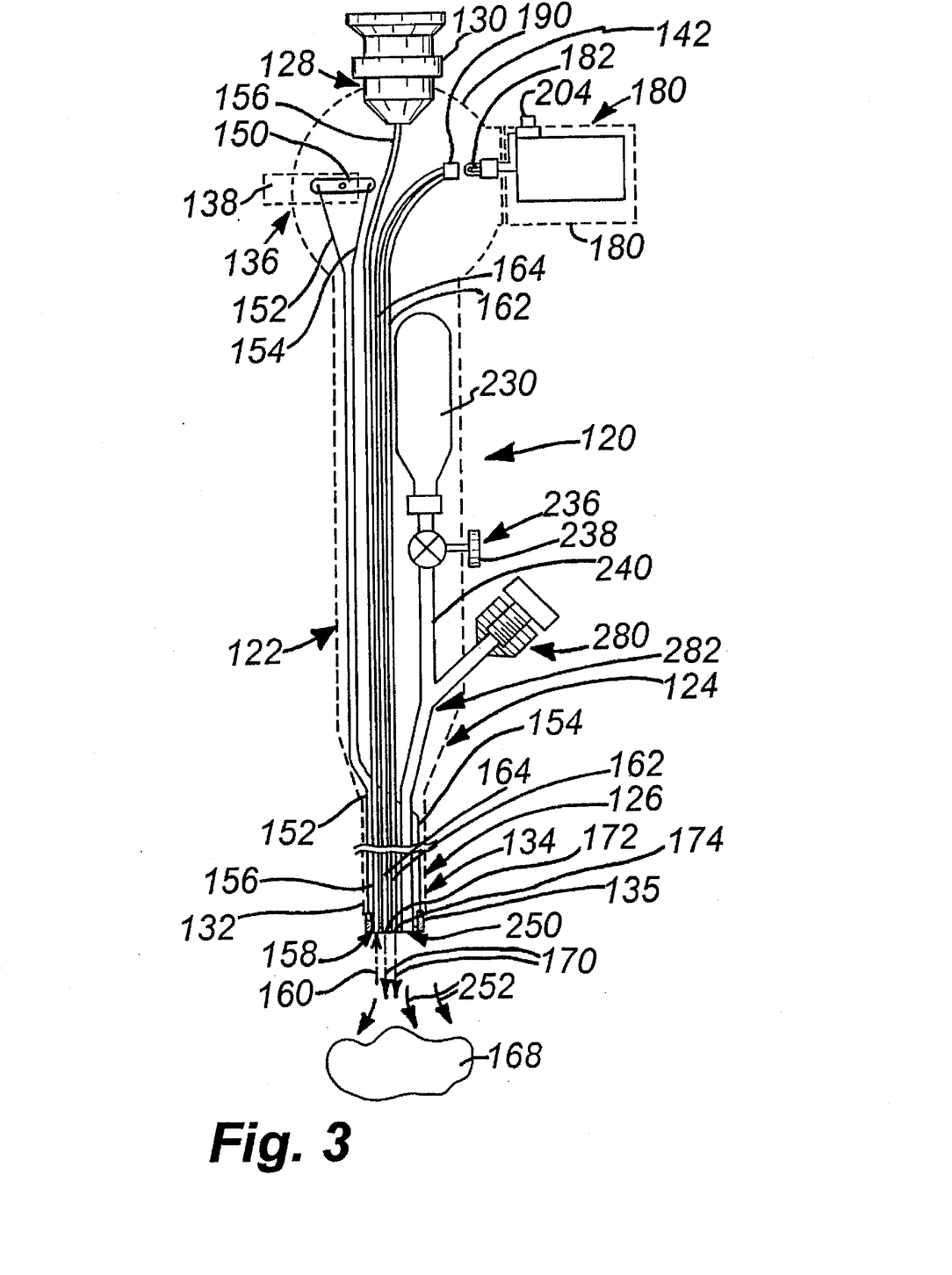
FIG. 3 is a somewhat schematic exposed side view of the cystoscope or endoscope of FIG. 2.
Figures 4, 5:
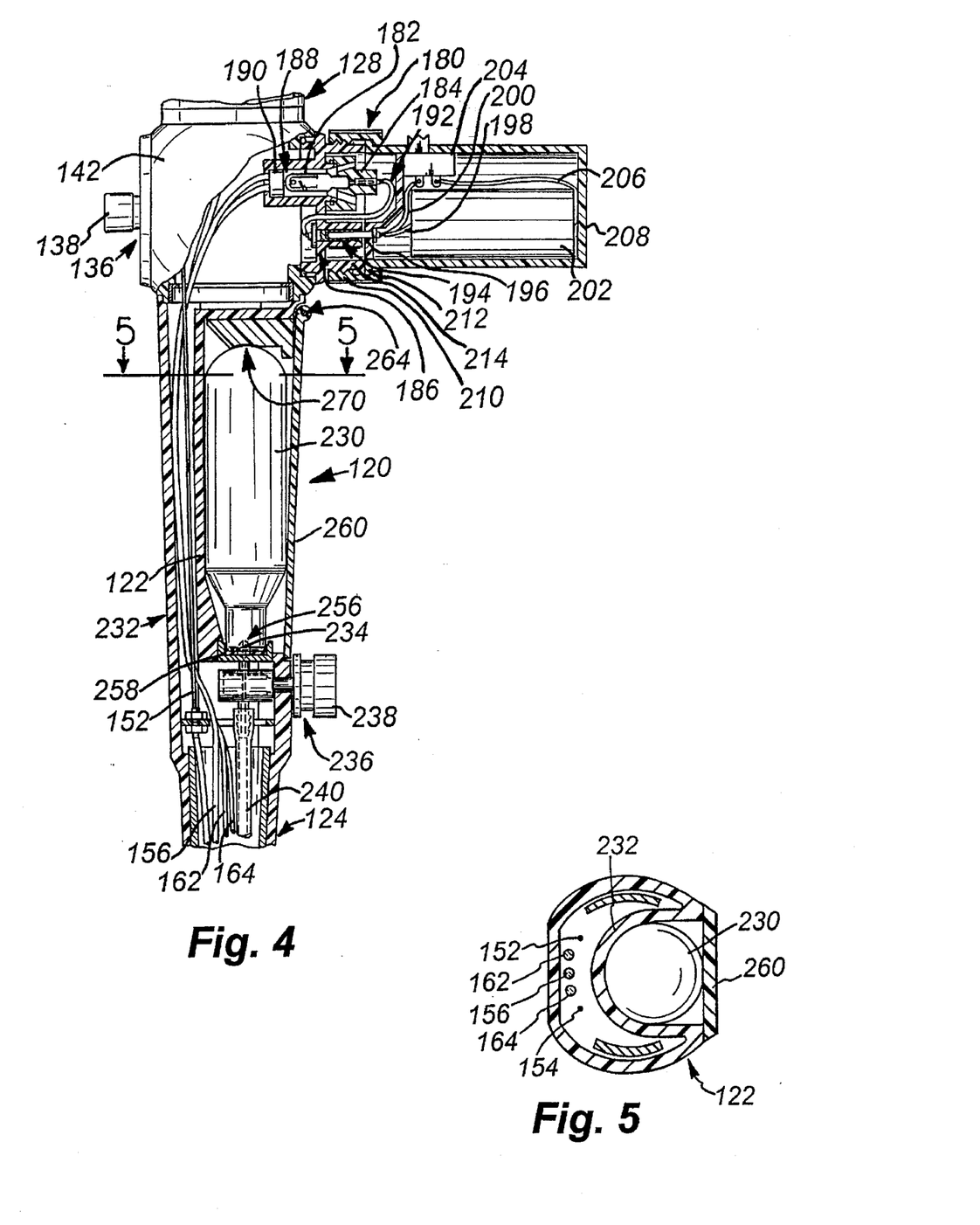
FIG. 4 is a partial side cross-section of the cystoscope or endoscope taken along line 4—4 of FIG. 2.
FIG. 5 is a top cross-section taken along line 5—5 of FIG. 4.

A steering control 136 including a movable steering control lever 138 is mounted on an enlarged ball section 142 of the housing 122. With further reference to FIGS. 3–5 the control lever 138 operates a clevis 150 interconnected with a pair of control cables 152 and 154. The control cables can comprise monofilament wires or braided metallic cables of conventional design. The cables 152 and 154 are interconnected with the tube 126 at the distal end 134 and enable the distal end 134 of the tube 126 to be bent or "steered" within at least one plane. The steerability permits the distal end 134 to negotiate bends in the urinary tract as the viewer moves the tube 126 down the urinary tract to its final destination. To steer the tube as it is driven down the urinary tract, the tube 126 is, typically, rotated by rotating the handle 122 to align the distal end 134 so that the plane of the bend in the distal end conforms with the bend encountered in the urinary tract. However, it is contemplated that the steering control 136 can include a second set of control cables enabling the distal end 134 of the tube 126 to be bent in three dimensions, rather than a single plane. In this instance, rotation of the handle and tube would, generally, be unnecessary. While not shown, the control lever 138 can include a lock for maintaining a predetermined bend in the distal end 134 of the tube 126.

The eye piece 128, which includes a series of focusing lenses (not shown) is optically connected with the viewing fiber optic cable 156. The viewing fiber optic cable 156, according to this embodiment, can comprise a group of bundled fiber optic strands of relatively small diameter so that the tube 126 remains substantially flexible. The bundles (not shown) present a composite image at the eye piece 128. The clarity of the image is sufficient for accurate examination of the viewed area or object 168 (FIG. 3). The distal end of the cable 156 typically includes a polished surface or small lens 158 formed within the polished end section 135. Viewed light from the object 168 enters the fiber optic cable 156 at the end 158 (see arrow 160 in FIG. 3).

Figure 6:
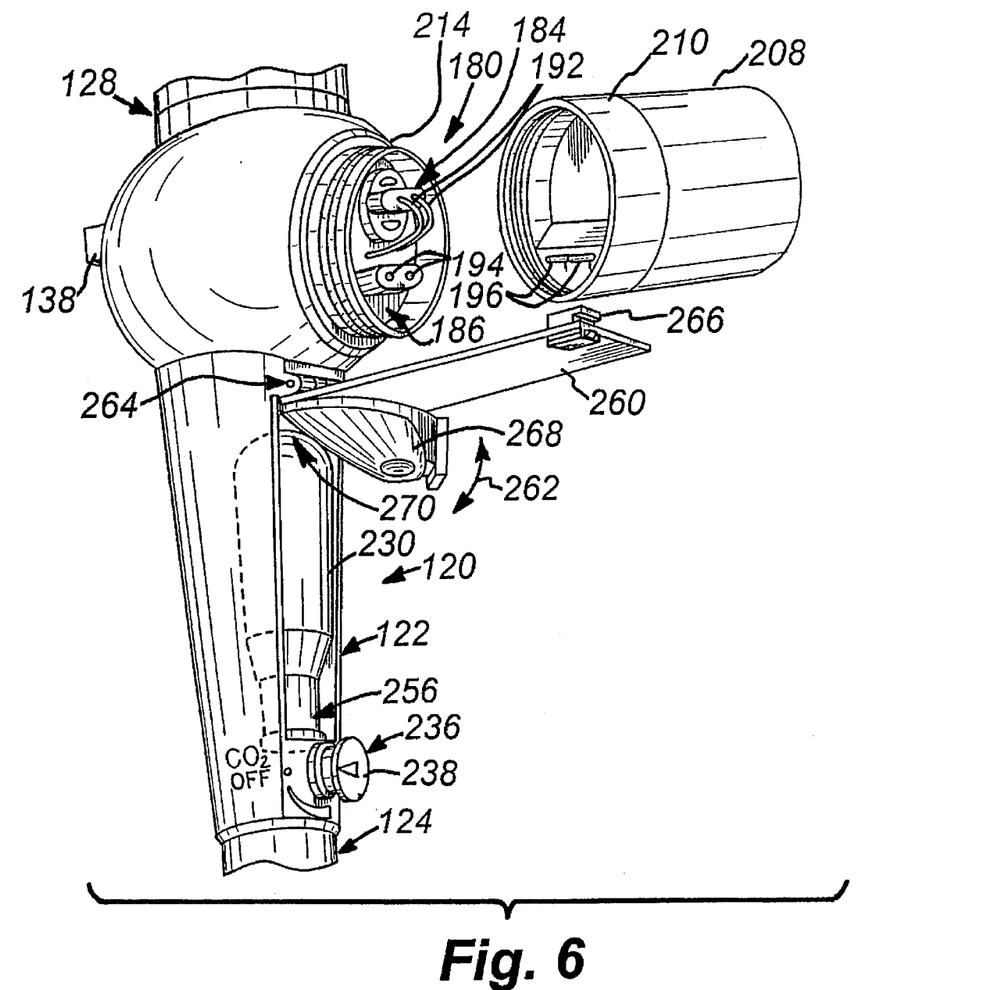
FIG. 6 is a perspective view of the cystoscope or endoscope of FIG. 2 with covers removed.

The cystoscope handle also includes a pair of illuminating fiber optic cables 162 and 164 that extend through the handle 122 and into the tube 126. The illuminating cables 162 and 164 terminate at the polished ring 135 and project light on the area or object 168 to be viewed (see arrows 170 in FIG. 3). The distal ends 172 and 174 of each illuminating fiber optic cable 162 and 164, respectively, can be polished, and/or can include an objective lens to provide a desired light spread. Unlike the prior art cystoscope detailed in FIG. 1, the cystoscope 120 of this embodiment includes a completely self-contained illumination source. The source 180 utilizes a high intensity incandescent light bulb having, for example, a rating of 150 watts. The bulb can be a halogen-type bulb for greater intensity and whiter light. With particular reference to FIGS. 4 and 6, the bulb is mounted in a socket 184 that is formed in the upper side wall 186 of the hand piece 122. The side wall 186 defines a cavity 188 into which the bulb projects. The side wall 186 is formed so that the illuminating fiber optic cables 162 and 164 penetrate into the bulb cavity 188. The cables terminate in a polished end structure 190 that enables clear transmission of light into the cables. The bulb socket 184 is connected by a pair of wires 192 to a two-prong plug socket 194 that is also formed in the upper housing side wall 186. The plug socket 194 is interconnected with a corresponding pair of plug prongs 196 that are each joined to a corresponding wire 198 and 200. One wire 198 interconnects directly with a battery 202, while the other wire 200 is connected to a single pole single throw switch 204 having another lead wire 206 interconnected with the battery 202. The battery 202, plug prongs 196 and switch 204 are self-contained within a removable housing 208 that is joined to the upper portion of the handle 122 by a threaded ring coupling 210 according to this embodiment. The threaded ring coupling 210 bears upon a circular shoulder 212 of the housing 208 and engages corresponding threads 214 formed on the upper portion of the handle 122.

Figure 7:
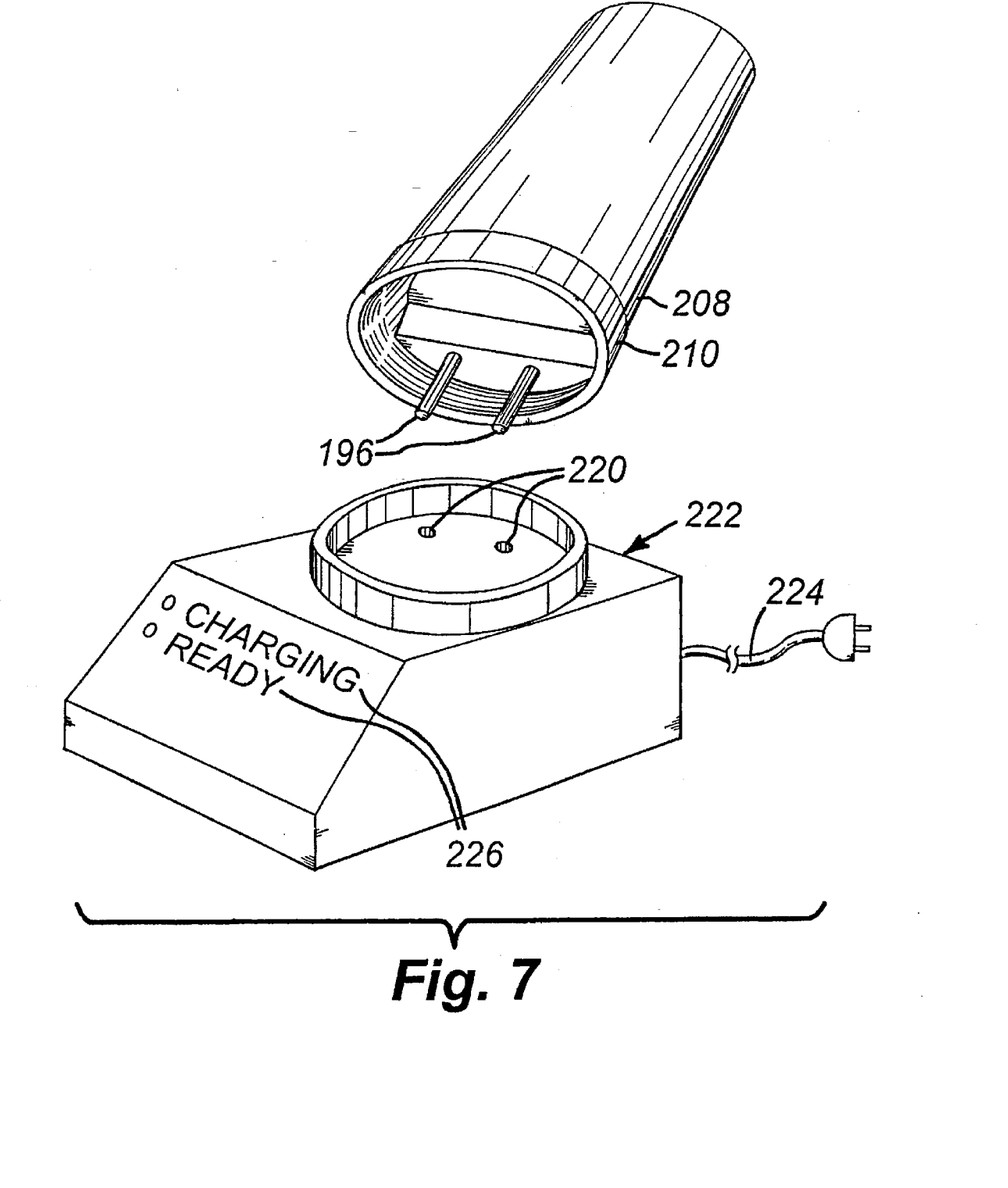
FIG. 7 is a perspective view of the cystoscope battery pack and charger according to this invention.

The battery, according to this embodiment, comprises a rechargeable nickel-cadmium or equivalent battery (a lithium-based battery, for example) such as those used in current-design oto/ophthalmoscopes. With further reference to FIG. 7, the housing 208 can be recharged at predetermined intervals by inserting the plugs 196 into corresponding receptacles 220 of a charging unit 222. The charging unit can include a transformer (not shown) for converting 110 VAC household current (power cord 224) into low voltage charging current. The charger 222 can include indicator lights 226 that report the status of the charging operation. It is contemplated, under normal use, that several 1–5 minute cystoscopic procedures can be undertaken with a single charge. By using rapid-charging batteries and a plurality of similar battery housings 208, procedures can continue indefinitely without interruption by exchanging depleted batteries for recharged batteries as needed and simultaneously recharging the depleted batteries.

It should be clear that a variety of battery housing configurations, switch locations and mounting systems can be utilized according to this invention. It is required only that a light be brought into contact with the illuminating fiber optic cables 162 and 164 housed within the handle 122. For example, a battery pack can be recessed into the handle 122 by reconfiguring the handle to receive an internally-mounted battery. Similarly, the cystoscope of this invention can be adapted to utilize the disposable commercial batteries when required. Additionally, the removable battery housing can be substituted with, or used in conjunction with, an electrical power lead interconnected with household current via, for example, a low voltage transformer (not shown). Such a transformer can provide auxiliary power and/or be used to recharge the battery without removing the pack from the unit.

As described above, the urinary tract and bladder are usually distended during a cystoscopic procedure by use of saline solution or sterile water. This technique necessitates a large quantity of fluid that is interconnected by sterile tubing to the prior art cystoscope. It has been recognized that insufflation of the urinary tract can be accomplished using a medical grade gas such as carbon dioxide ($CO_2$). $CO_2$ is currently used for organ insufflation in urologic instrumentation such as the cystometer which monitors bladder pressure, and in gastrointestinal endoscopy. These techniques, however, typically use an external source of carbon dioxide in conjunction with the necessary hand-held instruments.

The cystoscope 120 according to this embodiment incorporates a self-contained insufflation system consisting of an 8 gram cartridge of medical grade $CO_2$ 230 located within the housing 122. With reference to FIGS. 4–6, the housing includes an internal side wall 232 having a semicylindrical shape that conforms to the shape of the cartridge 230. The cartridge is arranged with its elongated direction parallel to the elongated direction of the housing 122. This arrangement most efficiently utilizes the available space in the handle or housing 122 without requiring substantial enlargement of the handle beyond the size normally employed according to the prior art. Accordingly, the handle is still readily gripable. The cartridge is located in fluid communication with a nipple 234 (FIG. 4) that is interconnected with a valve 236. The valve 236 includes an adjustment knob 238 that regulates the shutoff and volume of carbon dioxide transmitted therethrough. The valve 236 is joined to a pressure tube 240 that extends the length of the tube 126 to an outlet 250 located at the distal end 134 of the tube 126. The outlet 250 expels $CO_2$ (arrows 252 in FIG. 3) based upon operation of the valve 238. The nipple 234 is formed with a point so that it can puncture the thin-walled metallic seal normally found on the forward end 256 of a conventional $CO_2$ cartridge 230. An engaging gasket 258 that can comprise a rubber or similar soft, pliable material maintains a gas seal between the forward end 256 and the nipple 234. It is contemplated that a variety of techniques can be employed for maintaining the cartridge 230 in contact with the nipple 234. Likewise, a variety of techniques can be employed for causing the nipple 234 to puncture the cartridge front end 256. In this embodiment, the housing is formed with a movable cover 260 that pivots (curved arrow 262 in FIG. 6) on a hinge 264 between an open and closed position. The cover includes a latch 266 (FIG. 6) that maintains the cover in a closed position. The cover includes, at its upper end, a wedge section 268 that bears upon the upper end 270 of the cartridge 230 when the cover 260 is pivoted to a closed position as shown in FIGS. 4 and 5. The wedge section 268 is sized and arranged so that closing of the cover, with the wedge forced inwardly onto the top 270 of the cartridge 230 causes the cartridge to bear down onto the nipple 234, resulting in puncturing of the front end 256. The wedge 268 maintains the cartridge in a sealed relationship against the gasket 258.

The eight gram $CO_2$ cartridge contemplated according to this embodiment can be used for approximately five examinations. It is relatively inexpensive and easily replaced when exhausted. Once the procedure is completed, the inserted $CO_2$ can be expelled by the patient without adverse effects.

Since instruments, such as graspers and biopsy forceps, medicaments and small quantities of saline or water may still be required for treatment or enhancement of light transmission, a fitting 280 is provided adjacent the distal portion 124 of the housing 122. The fitting 280 can include a sealed disk for injection of fluid by syringe or can include a locking structure for joining a corresponding fitting on a feed tube. The fitting can also be adapted to receive a control cable from an instrument (not shown). In this embodiment, the fitting 280 is joined at a junction connection 282 (FIG. 3) to the insufflation tube 240. However, it is contemplated that a separate conduit can be provided along the tube 126 with a separate exit port at the distal end 134 of the tube 126.

As noted above, the portable cystoscope described herein can be modified for use as an endoscope or other viewing device in which illumination and/or irrigants are required. The cystoscope according to this invention has advantages over the prior art in that no external sources of irrigant and illumination are required. The resulting structure is, therefore, light weight, portable, and easy to set up and maintain, regardless of the examining location.

The foregoing has been a detailed description of a preferred embodiment. Various modifications and additions can be made without departing from the spirit and scope of this invention. As such, this description is meant to be taken only by way of example and not to otherwise limit the scope of this invention. For example, the robe of this invention can include a variety of actuable tools at its distal end in addition to the illumination and/or insufflation structure described herein.

What is claimed is:

1. A portable viewing device comprising:

a handle;

an elongated tube extending distally from the handle;

a viewing port located on the handle;

a viewing conduit in optical communication with the viewing port and extending to a distal end of the tube;

a light source mounted entirely on and carried by the handle;

a light conduit extending from the light source through the tube, constructed and arranged to project illuminating light from the distal end of the tube;

a gas cartridge interconnected with a valve located on the handle and a gas conduit extending from the valve through the tube to an outlet located at the distal end of the tube; and a door that selectively and fully encloses the gas cartridge within the handle and wherein the door is movable relative to the handle between an open position and a closed position, the handle including a puncturing nipple in communication with the valve and the gas conduit for puncturing the cartridge, the door including a base member that forces the cartridge onto the nipple when the door is moved to the closed position.

2. The viewing device as set forth in claim 1 wherein the viewing port comprises an eye piece.

3. The viewing device as set forth in claim 1 further comprising control cables extending from the handle to a location adjacent the distal end of the tube constructed and arranged for steering the end of the tube along at least one plane.

4. The viewing device as set forth in claim 1 further comprising an irrigation/instrument conduit extending from a portion of the handle through the tube to the distal end of the tube constructed and arranged to guide at least one of an instrument cable and liquid from a remote location to an outlet at the distal end of the tube.

5. The viewing device as set forth in claim 4 further comprising a junction interconnecting the irrigation/ instrument conduit with the gas conduit.

6. The viewing device set forth in claim 1 where the light source comprises a bulb and a battery interconnected with the bulb.

7. The viewing device set forth in claim 6 further comprising a housing removably interconnected with the handle and containing the battery.

8. The viewing device as set forth in claim 7 wherein the housing is constructed and arranged to be interconnected with a recharging unit when the housing is separated from and free of interconnection with the viewing device.

9. The viewing device as set forth in claim 1 wherein the light conduit comprises at least one fiber optic cable.

10. The viewing device as set forth in claim 1 wherein the viewing conduit comprises at least one fiber optic cable.

11. A cystoscope comprising:

an elongated handle having a proximal end and a distal end;

a viewing port located at the proximal end;

a tube extending from the distal end, constructed and arranged for placement in a body, the tube being flexible so as to conform to curved portions within the body;

a steering control located in the handle interconnected with steering cables that extend from the handle through the tube to a distal end of the tube remote from the handle, the steering controls and the steering cable being constructed and arranged so that movement of the cables by means of the steering control causes a bend to form in a portion of the tube;

a fiber optic light conduit extending from the viewing port to the distal end of the tube for transmitting viewed images from the distal end of the tube to the viewing port;

a fiber optic light conduit extending from a predetermined location on the handle to the distal end of the tube, constructed and arranged to project illuminating light at the distal end of the tube;

a light bulb, in optical communication with the fiber optic light conduit, mounted at the predetermined location on the handle and a battery electrically connected with the light bulb, the battery being mounted on the handle and being operable by a switch located on the handle; and a fluid conduit extending from the handle to the distal end of the tube in communication with a gas cartridge and a valve interconnected between the gas cartridge and the fluid conduit for delivering gas through the fluid conduit to the distal end of the tube at predetermined times and wherein the handle includes a compartment for receiving the cartridge so that the cartridge is enclosed by the handle and wherein the handle is grippable over the compartment.

12. The cystoscope set forth in claim 11 wherein the gas cartridge comprises a medical grade 8 gram $CO_2$ cartridge.

13. The cystoscope as set forth in claim 12 further comprising a closure structure for covering the compartment having the gas cartridge therein, a nipple for puncturing and sealing the cartridge in communication with each of the valve and the fluid conduit, and a movable base that forces the cartridge into engagement with the nipple.

14. A cystoscope comprising:

a handle having a proximal end and a distal end, the handle including a compartment thereon;

a viewing port located at the proximal end;

a flexible tube extending from the distal end, constructed and arranged for passage into a body;

a steering control located on the handle and steering cables interconnected with the steering control and passing from the handle into the tube the steering cables being attached adjacent a distal end of the tube wherein movement of the steering control causes an associated movement of the steering cables which causes a portion of the tube to define a predetermined curve to conform to a curve of the body;

a light source in communication with the handle, providing illuminating light to a fiber optic light conduit extending from the handle to a light outlet at a distal end of the tube;

a fiber optic viewing conduit that transmits viewed light from the distal end of the tube to the view port; and a fluid conduit extending from the compartment of the handle to the distal end of the tube and a gas cartridge located within the compartment on the handle and in communication with the fluid conduit, the gas cartridge being operable at predetermined times to deliver gas at the distal end of the tube for insufflation of a portion of the body adjacent the distal end of the tube.

15. The cystoscope as set forth in claim 14 further comprising a battery and a battery housing removably located on the handle and interconnected with the light source.

16. The cystoscope as set forth in claim 14 further comprising a closure structure for closing an open portion of the compartment so that a portion of the handle adjacent the closure structure is grippable.

17. The cystoscope as set forth in claim 16 wherein the gas cartridge includes a puncturable seal wherein the handle and further comprises a puncturing nipple in fluid communication with the fluid conduit for puncturing and forming a fluid tight connection with the puncturable seal upon placement of the cartridge onto the nipple.

18. The cystoscope as set forth in claim 17 further comprising a base structure for forcing the cartridge seal into engagement with the puncturing nipple at predetermined times.

* * * * *